(12) United States Patent
Chatlapalli et al.

(10) Patent No.: US 7,786,297 B2
(45) Date of Patent: Aug. 31, 2010

(54) PURIFIED FORM OF TANAPROGET

(75) Inventors: Ramarao Chatlapalli, Hopewell Junction, NY (US); Arwinder Nagi, Thiells, NY (US); John Potoski, West Nyack, NY (US); Jean Louise Helom, Hillsdale, NJ (US); Bogdan Kazimierz Wilk, New City, NY (US); Arkadiy Zinoviy Rubezhov, West Nyack, NY (US); Vladimir Dragan, Chester, NY (US)

(73) Assignee: Wyeth LLC, Madison, NJ (US)

( * ) Notice: Subject to any disclaimer, the term of this patent is extended or adjusted under 35 U.S.C. 154(b) by 818 days.

(21) Appl. No.: 11/412,016

(22) Filed: Apr. 26, 2006

(65) Prior Publication Data

US 2006/0247236 A1    Nov. 2, 2006

Related U.S. Application Data

(60) Provisional application No. 60/675,738, filed on Apr. 28, 2005.

(51) Int. Cl.
*C07D 265/14* (2006.01)
(52) U.S. Cl. ........................................ 544/92
(58) Field of Classification Search .................... 544/92
See application file for complete search history.

(56) References Cited

U.S. PATENT DOCUMENTS

| 6,436,929 | B1 | 8/2002 | Zhang et al. |
| 2003/0092711 | A1 | 5/2003 | Zhang et al. |
| 2004/0006060 | A1 | 1/2004 | Fensome et al. |
| 2004/0014798 | A1 | 1/2004 | Fensome et al. |
| 2006/0035843 | A1 | 2/2006 | Shen et al. |
| 2006/0142280 | A1 | 6/2006 | Zhang et al. |

FOREIGN PATENT DOCUMENTS

| WO | WO 00/66570 A1 | 11/2000 |
| WO | WO 2005/104711 A2 | 11/2005 |
| WO | WO 2005/105817 A2 | 11/2005 |

OTHER PUBLICATIONS

Rasenack et al. "Microcrystals for dissolution rate enhancement of poorly water-soluble drugs" 2003, International Journal of Pharmaceutics, 254, 137-145.*
Fensome et al., "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonists Tanaproget" J. Med. Chem., 48:5092-5095 (Jul. 12, 2005).
Zhang et al., "Novel 6-Aryl-1,4-dihydrobenzo[d][1,3]oxazine-2-thiones as Potent, Selective, and Orally Active Nonsteroidal Progesterone Receptor Agonists", Bioorg. & Med. Chem. Lett., 13:1313-1316 (2003).
Winneker et al., "Nonsteroidal Progesterone Receptor Modulators: Structure Activity Relationships" Seminars in Reproductive Medicine, 23(1):46 (2005).
Borka et al, Crystal Polymorphism of Pharmaceuticals, Acta Pharm. Jugosl., 40, pp. 71-94, (1990).
Bapst et al., "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.
Crabtree et al., "Development of a Mouse Model of Mammary Gland Versus Uterus Tissue Selectivity Using Estrogen- and Progesterone-Regulated Gene Markers", Journal of Steroid Biochemistry & Molecular Biology, vol. 101, (Sep. 2006; e-published Aug. 22, 2006), pp. 11-21.
Bapst et al., "Pharmacokinetics and Safety of Tanaproget, a Nonsteroidal Progesterone Receptor Agonist, in Healthy Women", Contraception, vol. 74 (Nov. 2006; e-published Sep. 15, 2006), pp. 414-418.
Bruner-Tran et al., "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", The Journal of Clinical Endocrinology & Metabolism, vol. 91, No. 4 (Apr. 2006; e-published Jan. 17, 2006), pp. 1554-1560.

* cited by examiner

*Primary Examiner*—James O Wilson
*Assistant Examiner*—Brian McDowell
(74) *Attorney, Agent, or Firm*—Howson & Howson LLP (57) ABSTRACT

Micronized tanaproget, purified tanaproget Form I, and micronized, purified tanaproget Form I are provided. Also provided are compositions containing one or more of the prepared tanaproget forms, methods of using one or more of the prepared tanaproget forms, and kits containing one or more of the prepared tanaproget forms.

13 Claims, 6 Drawing Sheets

PURIFIED FORM OF TANAPROGET

CROSS-REFERENCE TO RELATED APPLICATIONS

This application claims the benefit of the priority of U.S. Provisional Patent Application Ser. No. 60/675,738, filed Apr. 28, 2005.

BACKGROUND OF THE INVENTION

Intracellular receptors (IR) form a class of structurally related gene regulators known as "ligand dependent transcription factors". The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control compositions, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Tanaproget, 5-(4,4-dimethyl-2-oxo-1,4-dihydro-2H-3,1-benzoxazin-6-yl)-1H-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed in the art are other forms of tanaproget for use in pharmaceutical compositions.

SUMMARY OF THE INVENTION

In one aspect, micronized tanaproget Form I is provided.

In another aspect, purified tanaproget Form I is provided.

In a further aspect, a kit containing purified tanaproget Form I; and a carrier suitable for administration to a mammalian subject is provided.

In still another aspect, a reference standard of purified tanaproget Form I is provided.

In yet a further aspect, a method of preparing a pharmaceutical composition comprising purified tanaproget Form I is provided.

Other aspects and advantages are described further in the following detailed description of the preferred embodiments thereof.

DETAILED DESCRIPTION OF THE INVENTION

Pharmaceutical compositions containing micronized tanaproget Form I, purified tanaproget Form I, and micronized and purified tanaproget Form I are provided and discussed herein.

As used herein, the term "tanaproget" refers to 5-(4,4-dimethyl-2-thioxo-1,4-dihydro-2H-3,1-benzoxazin-6-yl)-1-methyl-1H-pyrrole-2-carbonitrile.

The term "purified" as used herein preferably refers to tanaproget that contains less than about 1% impurities. In one example, purified tanaproget contains less than about 0.5% impurities. In another example, purified tanaproget contains less than or equal to about 0.36% impurities. Desirably, purified tanaproget is about 99.5% pure.

The term "solvent" as used herein refers to a solvent in which tanaproget has acceptable, moderate, good, or complete solubility. Similarly, the term "anti-solvent" as used herein refers to a solvent in which tanaproget has limited, reduced, or no solubility.

A. Micronized Tanaproget

Tanaproget Form I can be micronized under nitrogen and conventional micronizing techniques, for example with a Trost or jet mill, applied to non-micronized tanaproget. One method of preparation of non-micronized tanaproget is described in U.S. Pat. No. 6,436,929, and generally in US Patent Application Publication No. US-2005-0272702-A1, which is hereby incorporated by reference. However, it is not limited to the method by which the non-micronized tanaproget Form I is produced.

Micronized tanaproget Form I typically has a median particle size of less than about 20 μm, desirably less than about 15 μm, and more desirably less than about 10 μm. Specifically, 90% of the particles are less than or equal to about 20 μm and 50% are less than or equal to about 15 μm as determined by the Malvern method, which is readily understood by one of skill in the art.

In one embodiment, the compositions are prepared by dry mixing micronized tanaproget, based upon the total weight of the unit dose, with the other components of the composition.

As referred to herein below, the term "wt/wt" refers to the weight of one component based on the total weight of the composition. Typically, this ratio does not include the weight of the capsule, the weight of any filler utilized in the capsule, and seal coating, if so utilized.

In one embodiment, micronized 5-(4,4-dimethyl-2-thioxo-1,4-dihydro-2H-3,1-benzoxazin-6-yl)-1-methyl-1H-pyrrole-2-carbonitrile Form I which has a particle size less than about 20 μm is provided.

B. Purification of Tanaproget

Also provided is purified tanaproget Form I that is more suitable for administration in a pharmaceutical composition. Typically, the unpurified tanaproget is micronized prior to purification.

The inventors have found that the purified tanaproget Form I provided herein is stable and less likely to convert to another polymorph during storage of either purified tanaproget Form I alone or in combination with other agents/excipients.

In one embodiment, tanaproget Form I is purified as described in US Patent Application Publication No. US-2005-0272702-A1, which is hereby incorporated by reference. However, it is not limited to the method by which the non-micronized tanaproget Form I is produced.

In another embodiment, tanaproget Form I is purified by recrystallization. The recrystallization can be performed using a solvent or solvent system. A number of solvents can be utilized to purify the tanaproget Form I and include ethyl acetate, acetone, or a combination thereof. Alternatively, solvent systems can be utilized in which one reagent of the system is a solvent capable of dissolving the tanaproget Form I and a second reagent of the solvent system is an anti-solvent. Desirable solvent/anti-solvent systems that are useful include, without limitation, acetone/tetrahydrofuran, acetone/methanol, acetone/toluene, and acetone/water. Desirably, tanaproget Form I is purified by recrystallization from acetone/water.

Typically, tanaproget Form I is purified by dissolving unpurified tanaproget in hot acetone to form a solution, the acetone solution is concentrated, water is mixed with the concentrated acetone solution, and the concentrated acetone/water solution is cooled to room temperature.

In a further embodiment, tanaproget Form I is dissolved in acetone and the solution is heated to about 45 to about 51° C. After circulating the heated solution through a carbon filter for at least about 4 hours, the filtered solution is concentrated using procedures known to those of skill in the art. After adding water to the concentrated solution, desirably at a rate which does not cool the refluxing acetone solution, the acetone/water solution is cooled to about −6 to about 0° C. Desirably, the acetone/water solution is cooled at a rate of less than about 0.5 ° C./minute. After holding the cooled solution at the reduced temperature for at least about 3 hours, the precipitated, purified tanaproget Form I is collected using filtration. The collected solid is washed with a water/acetone mixture, desirably washing the solid twice with a 1:1 water/acetone mixture. The washed purified tanaproget Form I is then dried at less than 35° C. for about 4 hours. Further drying at less than about 50° C. is performed to remove residual acetone/water as measured by spectroscopic methods.

Typically, the impurities still present in purified tanaproget Form I include residual acetone, isopropyl alcohol, or water. In one example, purified tanaproget Form I contains less than about 0.1% water. In another example, purified tanaproget Form I contains less than or equal to about 0.07% water.

In one embodiment, a purified Form I of 5-(4,4-dimethyl-2-thioxo-1,4-dihydro-2H-3,1-benzoxazin-6-yl)-1-methyl-1H-pyrrole-2-carbonitrile having a differential scanning calorimetry thermogram having an endotherm with a $T_{onset}$ at about 230° C.; and an X-ray diffraction peak pattern comprising peaks at 2θ of about 6.6°, 10.3°, 14.4°, 19.8°, 23.8°, 26.3°, and 29.1° is provided.

C. Characterizing Purified Tanaproget

Purified tanaproget Form I can be characterized using several spectroscopic techniques including nuclear magnetic resonance (proton and carbon), mass spectroscopy, infrared spectroscopy, chromatography such as high performance liquid chromatography, X-ray diffraction, and differential scanning calorimetry, among others. Desirably, the spectra obtained on purified tanaproget Form I using these techniques provide evidence that the purified tanaproget Form I contains less than 1% impurities.

Figure 1:
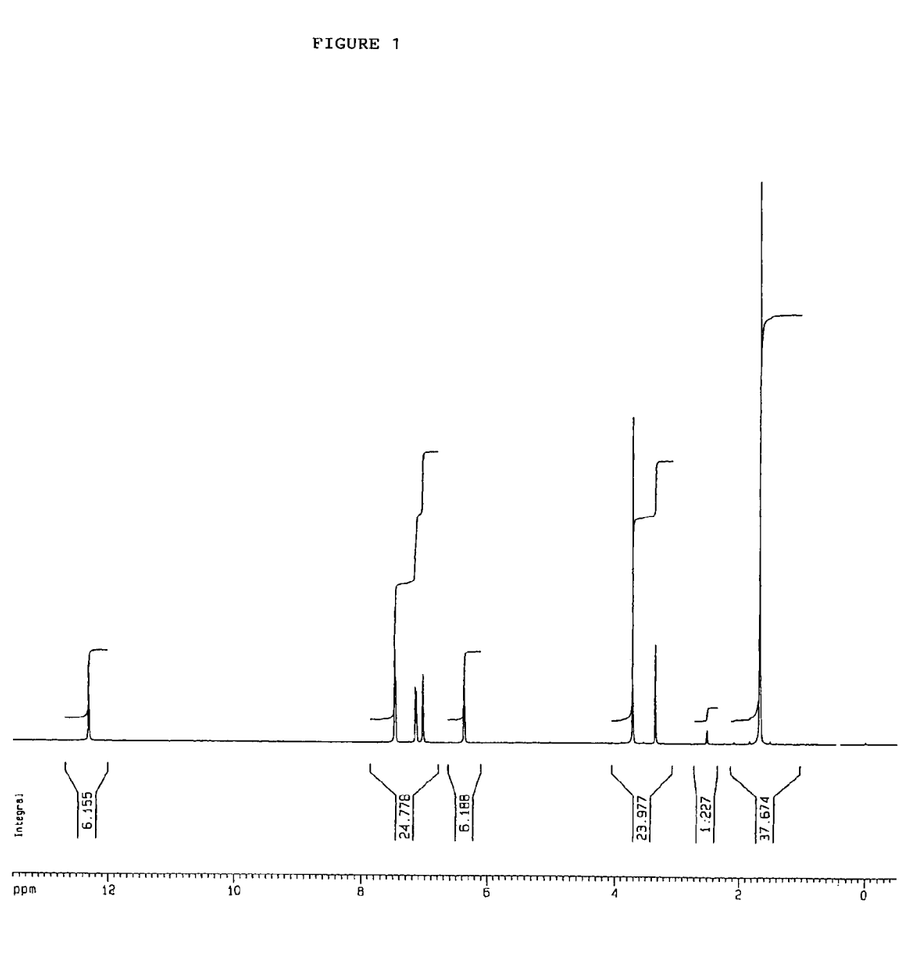
FIG. 1 provides the proton nuclear magnetic resonance spectrum of a sample of purified tanaproget Form I.

In one embodiment, purified tanaproget Form I provides a proton ($^1$H) nuclear magnetic resonance (NMR) spectrum of FIG. 1A and a carbon ($^{13}$C) NMR spectrum of FIG. 1B. Desirably, the $^1$H-NMR spectrum ($d_6$-dimethylsulfoxide) contains peaks at about δ 3.7, 7.0, 6.4, 7.5, 7.15, 7.5, 1.7, and 12.3. More desirably, the $^1$H-NMR spectrum ($d_6$-dimethylsulfoxide) contains peaks at δ 3.72 (s), 7.04 (d, J=4.0 Hz), 6.38 (d, J=4.0 Hz), 7.48 (m), 7.15 (d, J=8.4 Hz), 7.47 (m), 1.69 (s), and 12.31 (s). Desirably, the $^{13}$C-NMR spectrum ($d_6$-dimethylsulfoxide) contains peaks at δ 33.8, 104.8, 114.1, 119.5, 109.8, 139.0, 127.0, 124.0, 127.0, 131.7, 114.6, 129.3, 83.3, 27.2, and 182.8. More desirably, the $^{13}$C-NMR spectrum ($d_6$-dimethylsulfoxide) contains peaks at δ 33.79, 104.79, 114.12, 119.46, 109.75, 139.07, 126.97, 123.98, 127.00, 131.65, 114.57, 129.33, 83.26, 27.24, and 182.84.

Figure 2:
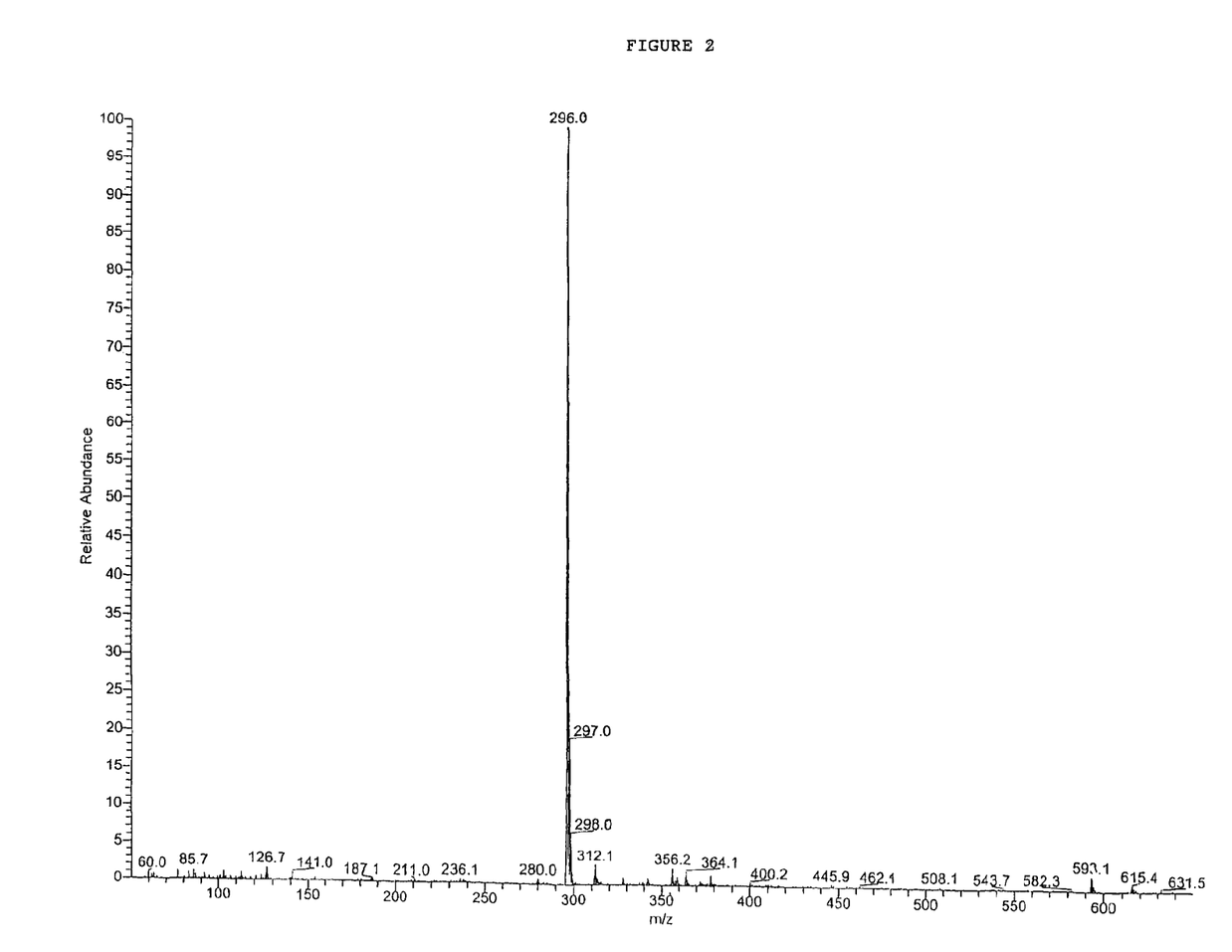
FIG. 2 provides the mass spectrum of a sample of purified tanaproget Form I.

In another embodiment, purified tanaproget Form I provides a mass spectrum (MS) having the spectrum of FIG. 2. The MS of purified tanaproget Form I thereby includes a [M-H] peak at 296.0.

Figure 3:
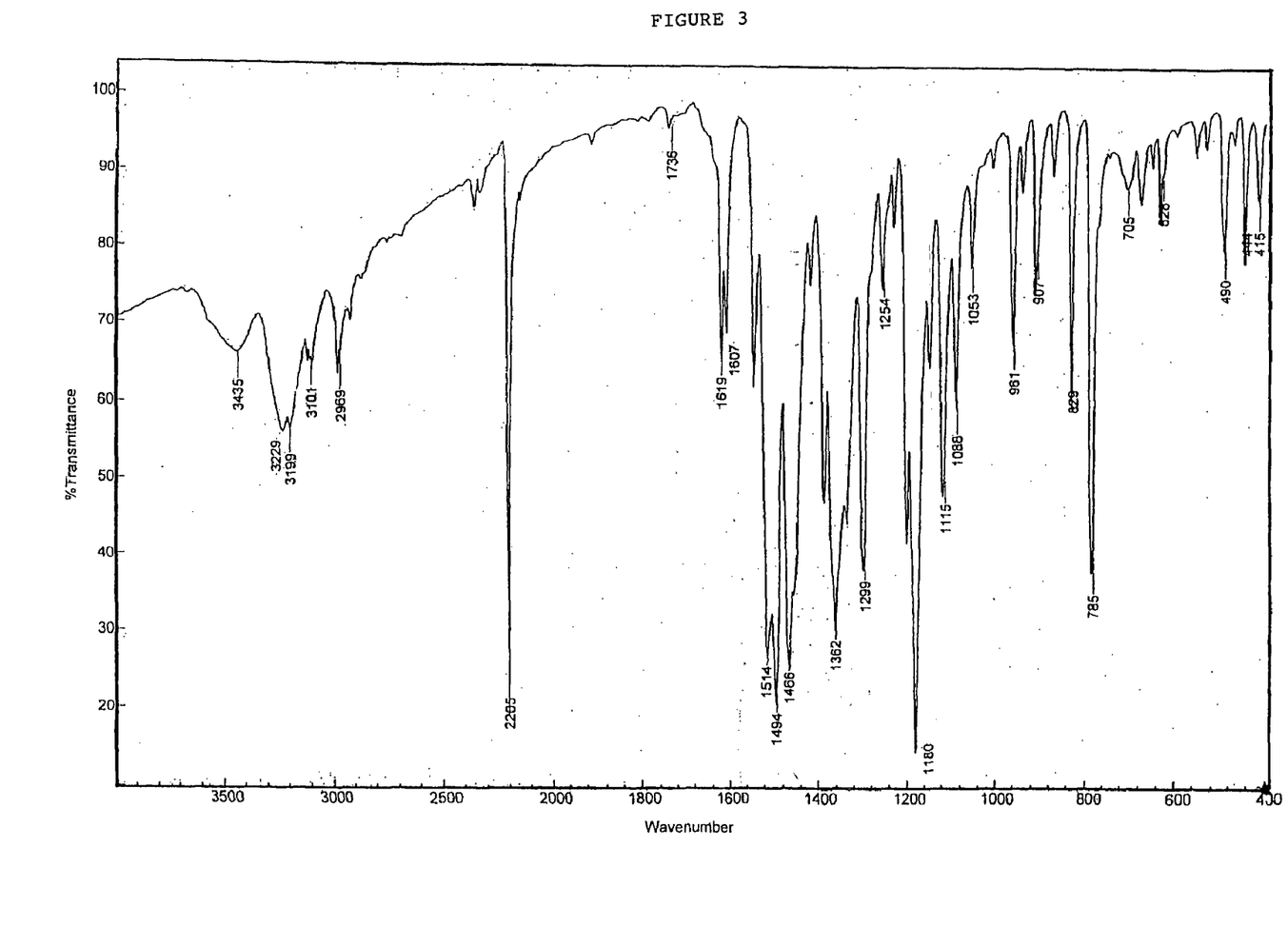
FIG. 3 provides the fourier transform infrared spectrum of a sample of purified tanaproget Form I.

In a further embodiment, purified tanaproget Form I provides a fourier transform infrared spectrum (IR) of FIG. 3.

Figure 4:
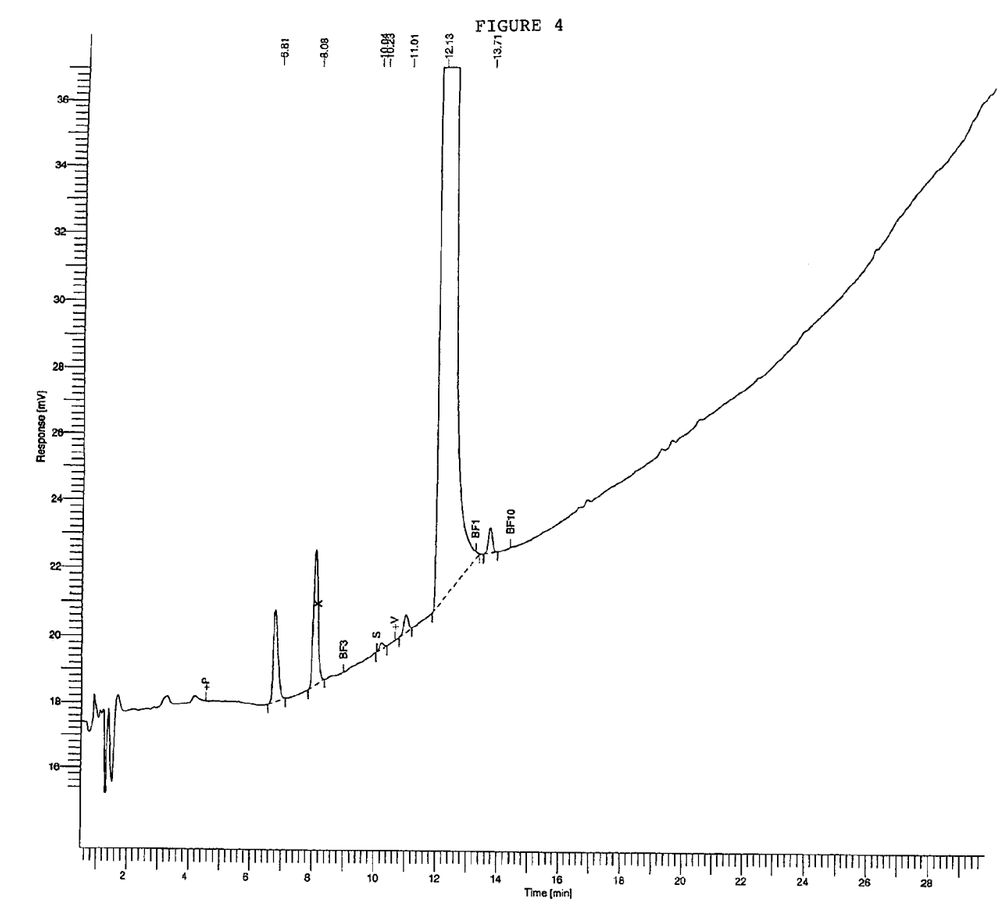
FIG. 4 provides the high performance liquid chromatography spectrum of a sample of purified tanaproget Form I.

In still another embodiment, purified tanaproget Form I provides a high performance liquid chromatography (HPLC) spectrum of FIG. 4. The HPLC spectrum thereby provides minor impurity peaks at t=0.56 min (0.10 %wt/wt), t=0.67 min (0.227% wt/wt), and t=1.13 min (0.025% wt/wt).

Figure 5:
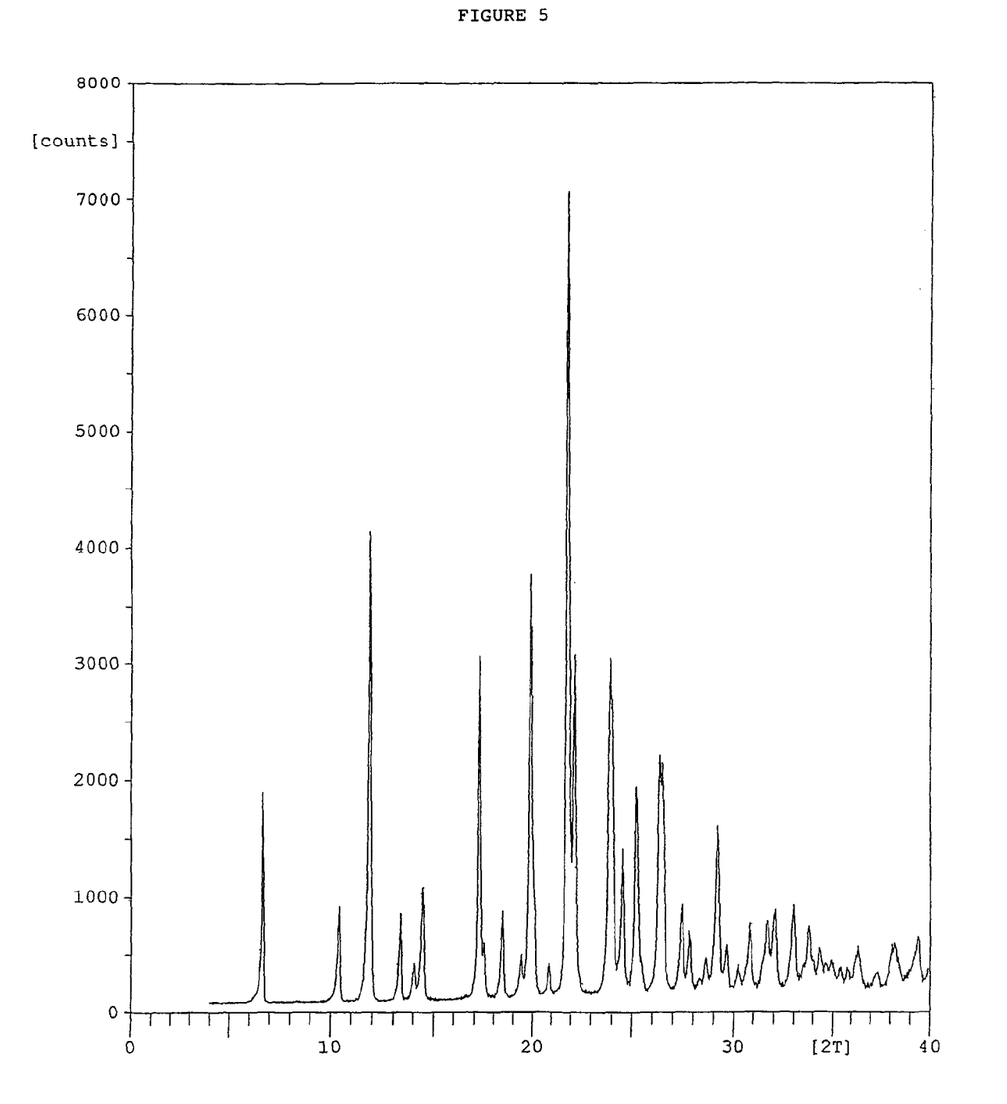
FIG. 5 provides the X-ray diffraction pattern of a sample of purified tanaproget Form I.

In yet a further embodiment, purified tanaproget Form I provides an X-ray diffraction pattern having the pattern of FIG. 5. The XRD includes an X-ray diffraction peak pattern including peaks at 2θ of about 6.6°, 10.3°, 14.4°, 19.8°, 23.8°, 26.3°, and 29.1°.

Figure 6:
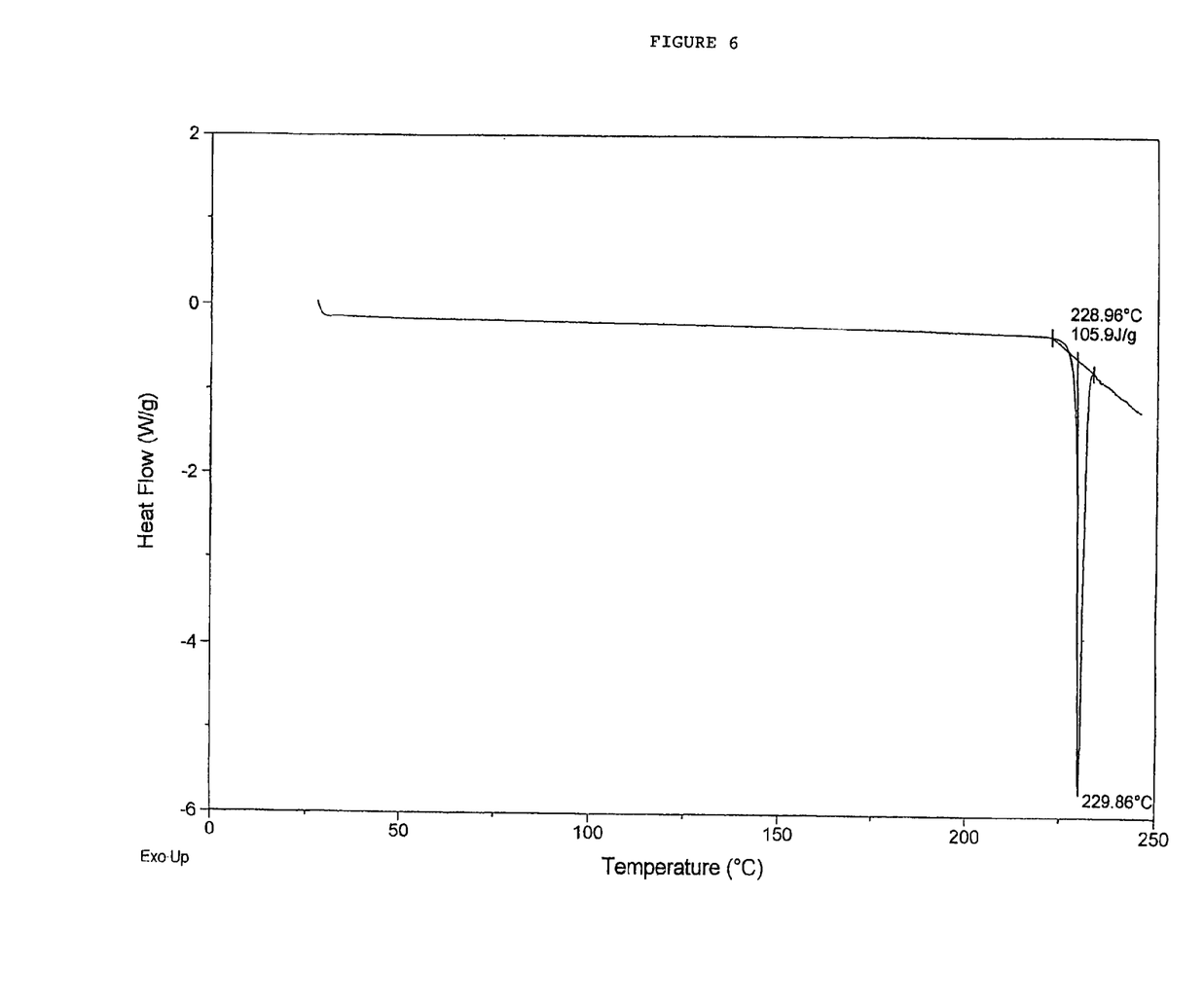
FIG. 6 provides the differential scanning calorimetry thermogram of a sample of purified tanaproget Form I.

In another embodiment, purified tanaproget Form I provides a differential scanning calorimetry (DSC) thermogram having the thermogram of FIG. 6. The DSC thermogram has an endotherm with a $T_{onset}$ at about 230° C.

In still a further embodiment, purified tanaproget Form I provides has a melting point of about 228 to about 231° C. Desirably, the melting point is about 229 to about 230° C. More desirably, the melting point is about 230° C.

D. Compositions Containing Purified Tanaproget

Also provided are compositions, preferably pharmaceutical compositions, containing purified tanaproget Form I alone or in combination with unpurified tanaproget. The compositions typically contain a pharmaceutically acceptable carrier, but can also contain other suitable components. Typically, the additional components are inert and do not interfere with the function of the required components of the compositions. The compositions can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl furamate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing purified tanaproget Form I to about 4 to about 6. In one embodiment, the pH of a solution containing purified tanaproget Form I is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used include mannitol, calcium phosphate, pregelatinized starch, or sucrose.

E. Methods of Using Purified Tanaproget

Further provided are methods of delivering purified tanaproget Form I to a patient, where the method includes administering purified tanaproget Form I.

The dosage requirements of purified tanaproget Form I may vary based on the severity of the symptoms presented and the particular subject being treated. Treatment can be initiated with small dosages less than the optimum dose of purified tanaproget Form I. Thereafter the dosage is increased until the optimum effect under the circumstances is reached. Precise dosages will be determined by the administering physician based on experience with the individual subject treated. In general, purified tanaproget Form I is most desirably administered at a concentration that will generally afford effective results without causing any unacceptable harmful or deleterious side effects. For example, an effective amount of purified tanaproget Form I is generally, e.g., about 0.05 mg to about 1 mg, about 0.05 mg to about 0.3 mg, about 0.05 mg, about 0.075 mg, about 0.1 mg, about 0.15 mg, about 0.2 mg, or about 0.3 mg.

Purified tanaproget Form I is therefore useful in contraception and hormone replacement therapy. Purified tanaproget Form I is also useful in contraception and the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors. Additional uses of purified tanaproget Form I include stimulation of food intake.

Purified tanaproget Form I can be formulated in any form suitable for the desired route of delivery using a pharmaceutically effective amount of purified tanaproget Form I. For example, purified tanaproget Form I can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

For example, purified tanaproget Form I may be formulated for administration orally in such forms as tablets, capsules, microcapsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like. The preferred pharmaceutical compositions from the standpoint of ease of preparation and administration are solid compositions, particularly tablets and hard-filled or liquid-filled capsules.

Purified tanaproget Form I may also be administered parenterally or intraperitoneally. Solutions or suspensions of purified tanaproget Form I as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms. Typically, such sterile injectable solutions or suspensions contain from about 0.05 to 5% suspending agent in an isotonic medium. Such pharmaceutical preparations may contain, for example, from about 25 to about 90% of the active ingredient in combination with the carrier, more usually between about 5% and 60% by weight.

In another embodiment, purified tanaproget Form I is delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile, stable under conditions of manufacture and storage, and free of the contaminating action of microorganisms such as bacteria and fungi.

The carrier can be a solvent or dispersion medium containing, for example, water, ethanol (e.g., glycerol, propylene glycol and liquid polyethylene glycol), oils, and mixtures thereof. Preferably the liquid carrier is water. In one embodiment, the oil is vegetable oil. Optionally, the liquid carrier contains a suspending agent. In another embodiment, the liquid carrier is an isotonic medium and contains 0.05 to about 5% suspending agent.

In a further embodiment, purified tanaproget Form I is delivered rectally in the form of a conventional suppository.

In another embodiment, purified tanaproget Form I is delivered vaginally in the form of a conventional suppository, cream, gel, ring, or coated intrauterine device (IUD).

In yet another embodiment, purified tanaproget Form I is delivered intranasally or intrabronchially in the form of an aerosol.

In a further embodiment, purified tanaproget Form I is delivered transdermally or by sustained release through the use of a transdermal patch containing purified tanaproget Form I and an optional carrier that is inert to purified tanaproget Form I, is nontoxic to the skin, and allows for delivery of purified tanaproget Form I for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release purified tanaproget Form I into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., purified tanaproget Form I, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. No. 4,295,987 and U.S. Pat. No. 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, purified tanaproget Form I can be formulated as described herein. See, U.S. Pat. Nos. 3,845,770; 3,916,899; 3,536,809; 3,598,123; and U.S. Pat. No. 4,008,719.

Preferably, purified tanaproget Form I is formed into a suitable dosing unit for delivery to a patient. Suitable dosing units include oral dosing units, such as a directly compressible tablets, capsules, powders, suspensions, microcapsules, dispersible powders, granules, suspensions, syrups, elixirs, and aerosols. Preferably, purified tanaproget Form I is compressed into a tablet, which is optionally added to a capsule, or purified tanaproget Form I is added directly to a capsule. Purified tanaproget Form I can also be formulated for delivery by other suitable routes. These dosing units are readily prepared using the methods described herein and those known to those of skill in the art.

Solid forms, including tablets, caplets, and capsules containing purified tanaproget Form I can be formed by dry blending purified tanaproget Form I with the components described above. In one embodiment, the capsules include hydroxypropyl methylcellulose, hypromellose capsule, or a hard shell gelatin capsule. The tablets or caplets that contain tanaproget are optionally film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of purified tanaproget Form I can vary depending on the other components of the composition being delivered, mode of delivery, severity of the condition being treated, the patient's agent and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

It is contemplated that when purified tanaproget Form I is used for contraception or hormone replacement therapy, it can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, purified tanaproget Form I can be administered in conjunction with one or more chemotherapeutic agents which can readily be selected by one of skill in the art.

F. Kits Containing Purified Tanaproget

Also provided are kits or packages containing purified tanaproget Form I. Kits can include purified tanaproget Form I or in combination with less pure forms and a carrier suitable for administration to a mammalian subject as discussed above. Typically, the tablets or capsules are packaged in blister packs, and preferably Ultrx™ 2000 blister packs.

The kits or packages containing purified tanaproget Form I are designed for use in the regimens described herein. These kits are preferably designed for daily oral delivery over 21-day, 28-day, 30-day, or 31-day cycles, among others, and more preferably for one oral delivery per day. When purified tanaproget Form I is to be delivered continuously, a package or kit can include purified tanaproget Form I in each tablet. When purified tanaproget Form I is to be delivered with periodic discontinuation, a package or kit can include placebos on those days when purified tanaproget Form I is not delivered.

Additional components may be co-administered with purified tanaproget Form I and include progestational agents, estrogens, and selective estrogen receptor modulators.

The kits are also preferably organized to indicate a single oral formulation or combination of oral formulations to be taken on each day of the cycle, preferably including oral tablets to be taken on each of the days specified, and more preferably one oral tablet will contain each of the combined daily dosages indicated.

In one embodiment, a kit can include a single phase of a daily dosage of purified tanaproget Form I over a 21-day, 28-day, 30-day, or 31-day cycle. Alternatively, a kit can include a single phase of a daily dosage of purified tanaproget Form I over the first 21 days of a 28-day, 30-day, or 31-day cycle. A kit can also include a single phase of a daily dosage of purified tanaproget Form I over the first 28 days of a 30-day or 31-day cycle.

In a further embodiment, a kit can include a single combined phase of a daily dosage of purified tanaproget Form I and a progestational agent over a 21-day, 28-day, 30-day, or 31-day cycle. Alternatively, a kit can include a single combined phase of a daily dosage of purified tanaproget Form I and a progestational agent over the first 21 days of a 28-day, 30-day, or 31-day cycle. A kit can also include a single combined phase of a daily dosage of purified tanaproget Form I and a progestational agent over the first 28 days of a 30-day or 31-day cycle.

In another embodiment, a 28-day kit can include a first phase of from 14 to 28 daily dosage units of purified tanaproget Form I; a second phase of from 1 to 11 daily dosage units of a progestational agent; and, optionally, a third phase of an orally and pharmaceutically acceptable placebo for the remaining days of the cycle.

In yet a further embodiment, a 28-day kit can include a first phase of from 14 to 21 daily dosage units of purified tanaproget Form I; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of purified tanaproget Form I; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of purified tanaproget Form I; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 µg levonorgestrel, a second phase of from 1 to 11 daily dosage units of purified tanaproget Form I; and optionally, a third phase of an orally and pharmaceutically acceptable placebo for the remaining days of the cycle in which no antiprogestin, progestin or estrogen is administered.

In a further embodiment, a 28-day kit can include a first phase of from 14 to 21 daily dosage units of a progestational agent equal in progestational activity to about 35 to about 100 µg levonorgestrel; a second phase of from 1 to 11 daily dosage units of purified tanaproget Form I; and optionally, a third phase of an orally and pharmaceutically acceptable placebo for the remaining days of the cycle in which no antiprogestin, progestin or estrogen is administered.

Preferably, the daily dosage of purified tanaproget Form I remains fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Preferably, the package has indicators for each day of the 28-day cycle, and more preferably is a labeled blister package, dial dispenser package, or bottle.

The kit can further contain instructions for administering purified tanaproget Form I.

G. Reference Standard

Further provided is a reference standard of purified Form I of 5-(4,4-dimethyl-2-thioxo-1,4-dihydro-2H-3,1-benzoxazin-6-yl)-1-methyl-1H-pyrrole-2-carbonitrile. Desirably, the reference standard is stable under conditions of manufacture and storage, and free of the contaminating action of microorganisms such as bacteria and fungi. The reference standard also optionally contains a solvent in which the purified Form I tanaproget is soluble, as described above. Desirably, the tanaproget Form I has acceptable, moderate, good, or complete solubility therein.

The reference standard is thereby useful for a variety of purposes. Specifically, the reference standard is useful for validation of a tanaproget Form I sample, determining the purity of a tanaproget Form I sample, standardization of a tanaproget Form I sample, quality control of a tanaproget Form I sample, and calibration of instruments for characterization of a tanaproget Form I sample, among others, using analytical techniques known to those of skill in the art. Analytical techniques that can utilize the reference standard include, without limitation, nuclear magnetic resonance (proton and carbon), mass spectroscopy, infrared spectroscopy, chromatography such as high performance liquid chromatography, X-ray diffraction, and differential scanning calorimetry, among others.

A kit containing a reference standard of purified Form I of 5-(4,4-dimethyl-2-thioxo-1,4-dihydro-2H-3,1-benzoxazin-6-yl)-1-methyl-1H-pyrrole-2-carbonitrile as previously described is also provided. The kits containing the reference standard optionally contain a solvent and/or instructions for performing the kit, among others.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Micronized Tanaproget

Tanaproget prepared according to U.S. Provisional Patent Application Ser. No. 60/647,656 and US Patent Application Publication No. US-2005-0272702-A1 was milled using a U-10 Comil mill and thereby micronized using a Jetmill® MC50 Jetpharma Micronizer with an E-Z™ FH-1.4 Feeder. Particle size was tested periodically for a particle size of less than about 15 µm, and desirably less than about 10 µm, being distributed throughout 50% of the sample. The micronized tanaproget was packed in triple poly-bagged fiber drums. A desiccant was inserted between the outermost bags and the atmosphere in the bags replaced with nitrogen gas.

Example 2

Purification of Tanaproget Using Solvents

Tanaproget containing residual palladium was dissolved in an aliquot of the solvent set forth in Table 1 at elevated temperatures and then cooled to reduced temperatures. After holding the batch at the reduced temperature for at least about 3 hours, the precipitated, purified tanaproget was collected using filtration and dried.

TABLE 1

| Solvent | Unpurified Tanaproget (g) | Purified Tanaproget (g) | Yield of Purified Tanaproget (%) | Purity of Purified Tanaproget (LC area %) |
|---|---|---|---|---|
| ethyl acetate | 2.02 | 0.89 | 44.1 | 99.0 |
| acetone | 2.05 | 1.08 | 52.8 | 98.4 |

Example 3

Purification of Tanaproget Using Solvent Systems

Tanaproget containing residual palladium was dissolved in an aliquot of acetone at elevated temperatures. An anti-solvent of Table 2 was then added to the acetone. After observing the cloudiness point, the batch was heated to elevated temperatures to achieve complete dissolution. The heating mantle was replaced with a cooling bath and the acetone/antisolvent solution was allowed to cool. After holding the batch at reduced temperatures for at least about 3 hours, the precipitated, purified tanaproget was collected using filtration and dried.

TABLE 2

| Antisolvent | Unpurified Tanaproget (g) | Purified Tanaproget (g) | Yield of Purified Tanaproget (%) | Purity of Purified Tanaproget (LC area %) |
|---|---|---|---|---|
| THF | 2.05 | 1.08 | 52.7 | 98.3 |
| methanol | 1.01 | 0.78 | 77.2 | 98.7 |
| toluene | 2.08 | 1.62 | 77.8 | 98.8 |
| water | 2.01 | 1.46 | 72.4 | 98.8 |

Example 4

Larger Scale Purification of Tanaproget Without Concentration

Tanaproget (250 g) containing residual palladium (21 ppm) was dissolved in acetone (2.3 L) at 46-50° C. After circulating the heated solution through a carbon filter for at least about 4 hours, the pump and transfer lines were rinsed into the reactor with acetone (400 mL). The combined acetone solution was heated to about 55 (±2° C.) and water (850 mL) was pumped in at the rate of 90 mL/min. After observing the cloudiness point, the batch was heated to reflux (57-60° C.) to achieve complete dissolution. The heating mantle was replaced with a cooling bath and the acetone/water solution was allowed to cool to about −6 to about 0° C. at a rate of less than about 0.5° C./minute. After holding the batch at the reduced temperature for at least about 3 hours, the precipitated, purified tanaproget was collected using filtration. The purified tanaproget was washed twice with a 1:1 water/acetone mixture (2×150 mL) and then dried at less than 35° C. for about 4 hours. Further drying at less than about 50° C.(5 torr vacuum) was performed to remove residual acetone/water (0.02%). The purified tanaproget weighed 192 g (76.8% yield, purity 99.42% by HPLC area%, mp 228-229° C., Pd<1 ppm).

Example 5

Larger Scale Purification of Tanaproget With Concentration

Tanaproget (83 g) was dissolved in acetone (820 mL) at 55° C. The solution was cooled to 45° C., Darco® G66 charcoal (4 g) was added and the mixture was re-heated to reflux and kept at reflux for 15 min. The batch was filtered through a layer of the Celite® reagent on a sintered glass funnel. The flask was rinsed with acetone (100 mL) and transferred onto the funnel. The filter cake was washed with acetone (3 ×150 mL). The combined filtrates were transferred into a distillation set and part of the solvent (800 mL) was collected. The concentrate was cooled to 55° C. and water (120 mL) was added dropwise while maintaining the temperature until a noticeable cloudiness was observed. The batch was re-heated to reflux to complete dissolution. The solution was allowed to cool down to ambient temperature. Crystallization was observed starting at about 40° C. The batch was cooled further to −5° C. and stirred at this temperature for 1 hour. The solids were filtered through a sintered glass and washed with 1:1 vol. acetone:water (2×50 mL). The cake was air-dried for 6 hours and further dried in a vacuum oven at 45° C. to a constant weight (67.2 g, 81% yield, purity 99.4% by HPLC area%, mp 229.2-230.5° C., Pd none detectable).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. An isolated, micronized form of 5-(4,4-dimethyl-2-thioxo-1,4-dihydro-2H-3,1-benzoxazin-6-yl)-1-methyl-1H-pyrrole-2-carbonitrile Form I having a median particle size less than about 20 µm prepared by micronizing purified Form I of 5-(4,4-dimethyl-2-thioxo-1,4-dihydro-2H-3,1-benzoxazin-6-yl)-1-methyl-1H-pyrrole-2-carbonitrile having:
   (i) a differential scanning calorimetry thermogram having an endotherm with a $T_{onset}$ at about 230° C.;
   (ii) an X-ray diffraction peak pattern comprising peaks at 2θ of about 6.6°, 10.3°, 14.4°, 19.8°, 23.8°, 26.3°, and 29.1°; and
   (iii) a melting point of 229 to 231° C.

2. The isolated, micronized form according to claim 1 which has a median particle size less than about 15 µm.

3. The isolated, micronized form according to claim 1 which has a median particle size less than about 10 µm.

4. The isolated, micronized form according to claim 1 which contains less than about 1% impurities.

5. The isolated, micronized form according to claim 4 which contains less than about 0.5% impurities.

6. The isolated, micronized form Form I according to claim 4, wherein the impurities comprise acetone, isopropyl alcohol, or water.

7. The isolated, micronized form according to claim 6 which contains less than about 0.1% water.

8. The isolated, micronized form according to claim 1, wherein the proton nuclear magnetic resonance spectrum comprises the spectrum of FIG. 1.

9. The isolated, micronized form according to claim 1, wherein the mass spectrum comprises the spectrum of FIG. 2.

10. The isolated, micronized form according to claim 1, wherein the fourier transform infrared spectrum comprises the spectrum of FIG. 3.

11. The isolated, micronized form according to claim 1, wherein the high performance liquid chromatography spectrum comprises the spectrum of FIG. 4.

12. The isolated, micronized form according to claim 1, wherein the X-ray diffraction pattern comprises the pattern of FIG. 5.

13. The isolated, micronized form according to claim 1, wherein the differential scanning calorimetry thermogram comprises the thermogram of FIG. 6.

* * * * *